(12) United States Patent
Hashimshony et al.

(10) Patent No.: US 9,301,734 B2
(45) Date of Patent: Apr. 5, 2016

(54) MEDICAL DEVICE AND METHOD FOR USE IN TISSUE CHARACTERIZATION AND TREATMENT

(75) Inventors: Dan Hashimshony, Givat Ada (IL); Gil Cohen, Jerusalem (IL)

(73) Assignee: DUNE MEDICAL DEVICES LTD., Caesarea (IL)

( * ) Notice: Subject to any disclaimer, the term of this patent is extended or adjusted under 35 U.S.C. 154(b) by 490 days.

(21) Appl. No.: 12/663,923

(22) PCT Filed: Jul. 13, 2008

(86) PCT No.: PCT/IL2008/000965
§ 371 (c)(1),
(2), (4) Date: Dec. 10, 2009

(87) PCT Pub. No.: WO2009/010960
PCT Pub. Date: Jan. 22, 2009

(65) Prior Publication Data
US 2010/0168611 A1 Jul. 1, 2010

(51) Int. Cl.
*A61B 17/00* (2006.01)
*A61B 18/14* (2006.01)
*A61B 19/00* (2006.01)
(Continued)

(52) U.S. Cl.
CPC ............ *A61B 10/0233* (2013.01); *A61B 5/00* (2013.01); *A61B 10/0266* (2013.01); *A61B 19/5225* (2013.01); *A61B 2017/00022* (2013.01); *A61B 2017/00128* (2013.01); *A61B 2017/00199* (2013.01); *A61B 2018/1475* (2013.01); *A61B 2019/461* (2013.01)

(58) Field of Classification Search
CPC .. A61B 10/0233; A61B 5/00; A61B 10/0266; A61B 19/5225; A61B 2019/461

USPC ............. 600/406–436, 547, 549, 564–568; 606/167–180
See application file for complete search history.

(56) References Cited

U.S. PATENT DOCUMENTS 5,846,513 A * 12/1998 Carroll et al. ............... 424/1.11
6,006,755 A * 12/1999 Edwards ..................... 128/898
(Continued)

FOREIGN PATENT DOCUMENTS

WO         9217108 A1    10/1992
WO    WO 98/12968 A1     4/1998
(Continued)

OTHER PUBLICATIONS

Office Action issued by the European Patent Office dated Nov. 25, 2011 in Application No. 08 776 603.6.
(Continued)

*Primary Examiner* — Sean Dougherty
(74) *Attorney, Agent, or Firm* — Browdy and Neimark, PLLC (57) ABSTRACT

A medical device is presented for use in tissue characterization and treatment. The device comprises: a tissue characterization probe comprising an elongated carrier carrying an array of tissue characterization sensors arranged in a spaced-apart relationship at least along an axis of said carrier, such that progression of the probe through a tissue mass provides for locating and determining a dimension of an abnormal tissue specimen inside said tissue mass based on characterization signals from the sensors in the array, thereby enabling consequent treatment of the abnormal tissue specimen by a treatment tool.

24 Claims, 4 Drawing Sheets

(51) Int. Cl.
*A61B 10/02* (2006.01)
*A61B 5/00* (2006.01)

(56) References Cited

U.S. PATENT DOCUMENTS

| | | | | |
|---|---|---|---|---|
| 6,120,437 | A * | 9/2000 | Yoon et al. | 600/204 |
| 6,321,109 | B2 * | 11/2001 | Ben-Haim et al. | 600/424 |
| 6,331,166 | B1 | 12/2001 | Burbank et al. | |
| 6,419,635 | B1 * | 7/2002 | Hedengren et al. | 600/549 |
| 6,419,640 | B1 * | 7/2002 | Taylor | 600/564 |
| 6,440,147 | B1 * | 8/2002 | Lee et al. | 606/159 |
| 6,689,145 | B2 | 2/2004 | Lee et al. | |
| 6,813,515 | B2 | 11/2004 | Hashimshony | |
| 7,122,011 | B2 | 10/2006 | Clifford et al. | |
| 7,184,824 | B2 | 2/2007 | Hashimshony | |
| 8,413,582 | B1 | 4/2013 | Chen | |
| 2001/0047169 | A1 | 11/2001 | McGuckin, Jr. et al. | |
| 2002/0019597 | A1 | 2/2002 | Dubrul et al. | |
| 2002/0035361 | A1 | 3/2002 | Houser et al. | |
| 2003/0009110 | A1 * | 1/2003 | Tu et al. | 600/547 |
| 2003/0050574 | A1 | 3/2003 | Krueger | |
| 2003/0055423 | A1 * | 3/2003 | Levinson | 606/47 |
| 2003/0138378 | A1 | 7/2003 | Hashimshony | |
| 2004/0255739 | A1 | 12/2004 | Clifford et al. | |
| 2005/0203419 | A1 | 9/2005 | Ramanujam et al. | |
| 2010/0168611 | A1 | 7/2010 | Hashimshony et al. | |
| 2013/0177972 | A1 | 7/2013 | Green et al. | |

FOREIGN PATENT DOCUMENTS

| | | |
|---|---|---|
| WO | WO 99/44506 A1 | 9/1999 |
| WO | 0174252 A2 | 10/2001 |
| WO | 2006103665 A2 | 10/2006 |
| WO | 2007015255 A2 | 2/2007 |
| WO | 2007083310 A2 | 7/2007 |
| WO | WO 2011/016035 A1 | 2/2011 |
| WO | WO 01/82998 A2 | 11/2011 |

OTHER PUBLICATIONS

Jan. 24, 2013 Search Report issued in EP Application No. 12168882.4.

International Search Report and Written Opinion dated Mar. 23, 2009 in corresponding International Application No. PCT/IL2008/000965.

* cited by examiner

MEDICAL DEVICE AND METHOD FOR USE IN TISSUE CHARACTERIZATION AND TREATMENT

FIELD OF THE INVENTION

This invention relates to medical devices and methods for use in tissue characterization and treatment.

BACKGROUND

Techniques for in situ identifying abnormal (e.g. tumorous) cells in a biological tissue are generally known. Such techniques include those utilizing determination of the electrical properties of a tissue, for example, by determination of electrical impedance or dielectric constants. Some kinds of tumors can be identified by determining differences in the measured electrical properties of the tissue. The identified and located region of abnormal tissue can then be treated and/or removed from the body Various types of tissue characterization sensor and its integration with a tissue treatment/removal tool are described in the following patent publications, all assigned to the assignee of the present application: US2003138378, WO2006103665, WO2007015255, U.S. Pat. No. 6,813,515 and U.S. Pat. No. 7,184,824.

Also, various techniques are known for removing a certain tissue specimen from a tissue mass. These techniques are disclosed for example in U.S. Pat. No. 6,689,145 and U.S. Pat. No. 7,122,011.

GENERAL DESCRIPTION

There is a need in the art to facilitate precise location and determination of a volume of a tissue specimen (e.g. abnormal tissues) to be treated (e.g. removed). Also, there is need in the art for a tissue treatment technique capable of adjusting a treatment volume to the determined volume of the abnormal tissue specimen.

The present invention solves the above problems by providing a novel medical device for use in tissue characterization and treatment. The device comprises a tissue characterization probe comprising an elongated carrier for carrying an array of tissue characterization sensors arranged in a spaced-apart relationship at least along an axis of said carrier. During the progression of the probe through a tissue mass, signals from the tissue characterization sensors are used for locating and determining a dimension of an abnormal tissue specimen inside the tissue mass. This enables consequent treatment of the abnormal tissue specimen by a treatment tool.

In preferred embodiment of the invention, the treatment tool is mounted on the characterization probe carrier. The treatment tool may be configured for carrying out at least one of the following biopsy, cutting, delivering physical treatment, delivering treatment medication, diagnostics.

Preferably, the treatment tool is selectively shiftable between its inoperative position being located substantially entirely inside the carrier and its operative position projecting by its at least one tissue treating portion towards outside the carrier. In preferred embodiments of the invention, the dimension of the tissue treating portion(s) projectable from the carrier, and possibly also location of the tissue treating portion(s) with respect to the carrier can be controllably varied.

In some embodiments of the invention, the probe carrier is formed with a guiding cutting tool, to facilitate insertion of the probe to a targeted location in the tissue. Also, in some embodiments of the invention, a marker may be left in the body, at the location of the treated (removed) tissue.

The invention also provides a novel method for use in tissue characterization and treatment. A tissue mass is scanned with an array of tissue characterization sensors arranged in a spaced-apart relationship along a scanning axis, and signals from the sensors are detected and analyzed while scanning locate and determine a dimension of an abnormal tissue specimen inside said tissue mass that is to be treated during progression of the array through the tissue mass.

Additionally, the invention provides a system for use in tissue characterization and treatment. The system comprises a medical device and a control unit connectable to the medical device. The latter is configured as described above, namely comprises a tissue characterization probe having a carrier on which an array of tissue characterization sensors is mounted with the sensors being arranged in a spaced-apart relationship at least along an elongated axis of the carrier. The control unit is configured for receiving and analyzing tissue characterizing signals from each of all the sensors and utilizing data indicative of the respective sensors' location, for determining a dimension of an abnormal tissue specimen.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
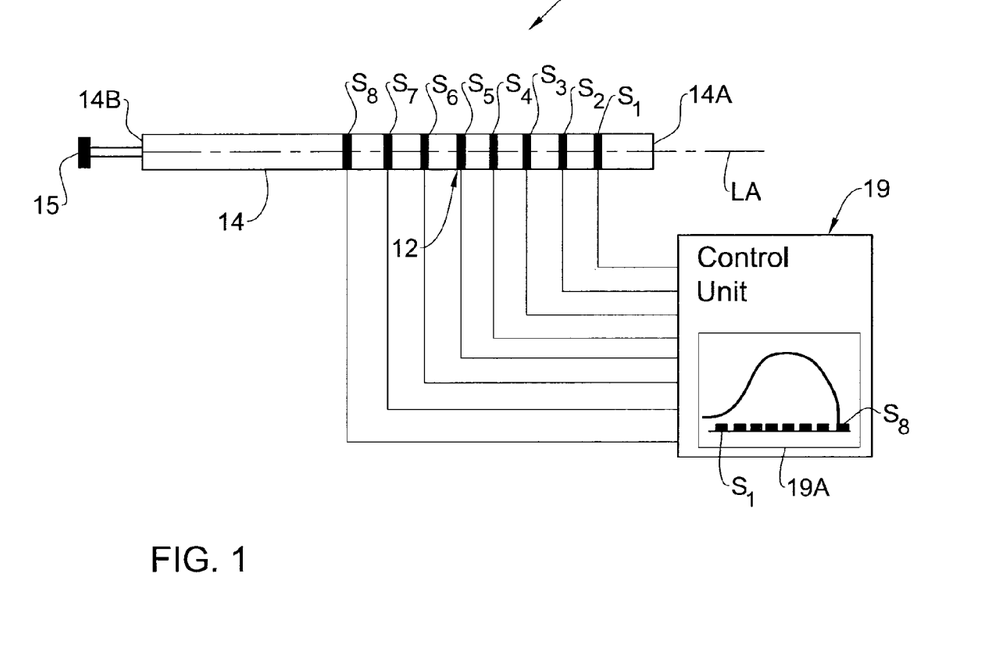
FIG. 1 is a schematic illustration of a medical device of the present invention.

Referring to FIG. 1, there is schematically illustrated a medical device, generally designated 10, according to an embodiment of the invention. The device 10 is configured for use in tissue characterization and treatment, and includes a tissue characterization probe 12 carried by an elongated shaft 14, which has distal and proximal ends 14A and 14B, respectively, and is formed with a control handle 15 at its proximal end 14B. The tissue characterization probe 12 includes an array of tissue characterization sensors, eight such sensors $S_1$-$S_8$ being shown in the present example.

The tissue characterization sensor array may include one or more of optical, radiofrequency (RF), microwave (MW), electrical, magnetic, temperature, elastic, biological, chemical, radioactive-emission, and mechanical sensors of any known type. The construction and operation of the tissue characterization sensor does not form part of the present invention, and therefore need not be specifically described. For example, sensors described in the above indicated patent publications assigned to the assignee of the present application may be used.

The sensors $S_1$-$S_8$ are arranged in a spaced-apart relationship along a longitudinal axis LA of the carrier 14, and may be arranged in one- or two dimensional array. For example, the sensor array may include, in addition to a group of sensors arranged in one-dimensional array, sensors arranged in a spaced-apart manner along a circumferential region of the carrier. The sensor array gives, in real time, indication about the nature of tissue along the carrier 14.

The sensors are spaced along the axis LA from one another a known distance, which may or may not be equal for all the sensors in the array. The known relative locations of the sensors along the carrier 12 allows for identifying corresponding locations in a tissue mass when the probe is progressing through the tissue mass (i.e. scans the tissue) based on signals received from the sensors. In this connection, the medical device 10 is associated with an appropriate control system 19 configured for receiving and analyzing the signals generated by the sensors. It should be understood that connection between the sensors and the control unit is shown in the figure schematically, and in case wired connection is used such wires would extend inside the shaft 14 and exit at the proximal end 14B.

The control system may be an external system connectable (via wires or wireless signal transmission) to the sensors, or may be a constructional part of the probe itself. The control system, based on the analysis of the received signals, operates for determining a location of the margins of an abnormal tissue region inside the examined tissue mass and generating output data indicative of a dimension of the abnormal tissue region. This allows for consequent treatment of the abnormal tissue region by an appropriate treatment tool.

The control system preferably includes a graphical user interface (GUI) 19A, and is configured for presenting information related to the signals received from each of the sensors. This information provides the operator with information regarding the tissue type at the locations of the sensors. The information presented on the GUI may assist the operator in analyzing the location and extent of the tissue to be treated.

Generally, the treatment tool may be configured for carrying out one or more of the following: biopsy, cutting, delivering physical treatment, delivering treatment medication, diagnostics. More specifically, the present invention is used for removal of an intact tissue specimen (abnormal tissue) and is therefore described below with respect to this specific but not limiting example.

Preferably, the probe 12 also carries a treatment tool, e.g. a cutting tool. This is implemented by configuring the probe such that the treatment tool can be selectively shiftable between its inoperative position, when it is located substantially entirely inside the carrier 14, and its operative positions when its one or more excision elements (constituting one or more tissue treating elements) project(s) from the carrier.

In some examples of the invention, the selective projection of the excision element is achieved by using the treatment tool of a kind known in the art, where the excision element projects from the carrier body through an opening made along the body portion while moving with respect to the carrier along an axis inclines with respect to the axis LA. In some other examples, the excision element projects from the carrier (e.g. from its distal end) while moving with respect to the carrier substantially along the axis LA. Such configurations are also generally known in the art. The treatment tool may be configured with a removed tissue collecting unit, which may or may not be selectively projectable from the probe.

According to the invention, the medical device is configured such that a dimension of the excision element part projecting from the carrier can be controllably adjusted (varied) in accordance with the determined dimension of the abnormal tissue margins, thereby adjusting the excision volume. Preferably, the excision element is configured for both cutting the tissue and collecting the tissue being cut.

The following are some specific but not limiting examples of the configuration of the device of the present invention. The same reference numbers are used for identifying components that are common in all the examples.

Figure 2:
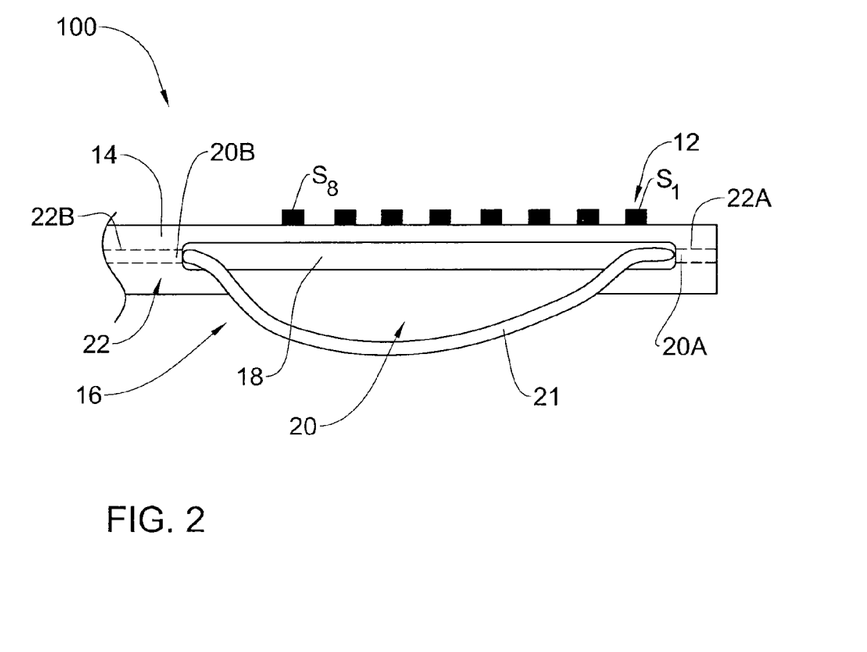
FIGS. 2 to 6 show five, examples, respectively, of the device configuration for both the tissue characterization and removal of a tissue specimen.

FIG. 2 shows a medical device 100 for removal of an intact tissue specimen. The device 100 includes an elongated shaft/ carrier 14 on which sensors $S_1$-$S_8$ of a tissue characterization probe 12 are mounted in spaced-apart locations, and a tissue cutting tool (generally, a treatment tool) 16 mounted on the carrier 14.

The cutting tool 16 has a body portion 22 located inside the carrier 14, and an excision element 20 projectable from the body 22 through an opening 18 made in the carrier 14 In the figure, the excision element 20 is shown in its operative projecting state. The excision element has a cutting edge 21, and may be configured to have a cup-like shape when in the projecting state, thereby enabling collection of tissue while being cut during the rotation of the carrier 14 and thus of the excision element 20.

The excision element 20 extends between its first and second ends 20A and 20B which are attached to respective first and second locations on the treatment tool body 22 and spaced-apart along the axis LA of the carrier 14. The treatment tool is configured to enable a controllable change of the dimensions of the excision element 20. In the present example, this is implemented by making the treatment tool body 22 from two spaced members 22A and 22B, where at least one of them is slidable with respect to the other along the carrier axis LA. As a result, a distance between the first and second locations, and accordingly the first and second ends 20A and 20B of the excision element, changes, thereby enable adjustment of the dimension of the cutting portion 21 projecting through the carrier 14.

By controlling the location of the excision element distal and proximal ends 20A and 20B along the carrier 14, and thus controlling the excision volume, a user can perform optimal removal of a tissue specimen, for example during a breast biopsy procedure. The entire excision element 20 may be movable along the body 22. Thus, the excision volume is controlled by user by changing the location of the excision element 20 along the carrier 14 and changing a distance between the distal and proximal ends of the excision element.

Figure 3:
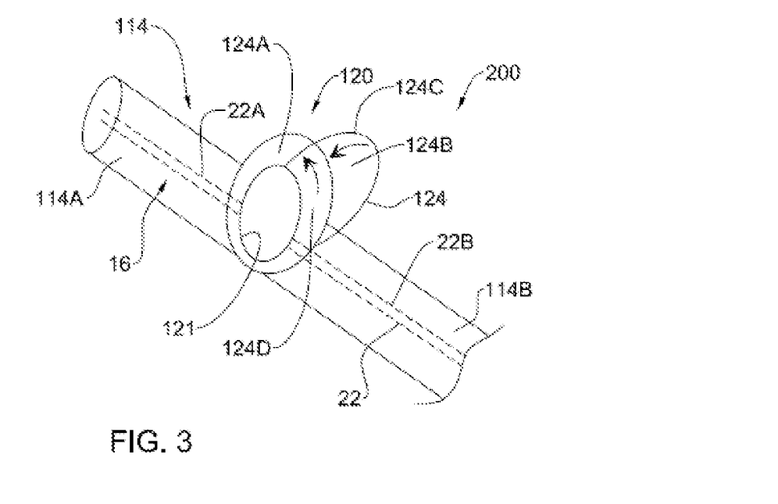

In the above example, the tissue removal procedure is carried while rotating the carrier 14. Such procedure can be performed while keeping the carrier position and rotating the treatment tool. This is exemplified in FIG. 3. A device 200 includes a carrier 114 formed by two separate parts 114A and 114B kept together by a treatment tool 16 inside the carrier 114. The treatment tool 16 has a body part 22 formed by two spaced-apart members 22A and 22B, and an excision element 120 attached thereto by its distal and proximal ends 20A and 20B. The excision element 120 has a semi-spherical surface 124 defining a cutting edge 21. The surface 124 has two arc-like portions 124A and 124B movable along the axis LA such that when they move towards one another one of the portions 124A becomes received by the other portion 124B. Also, the surface 124 has two parts 124C and 124D separately movable such that portion 124C can be received by portion 124C. These movements allow for altering the excision volume when in the operative projecting state of the excision element 120 and for shifting the element 120 between its operative projecting position and its inoperative position being located inside the carrier 14. Cutting is implemented while rotating the tool body 22 with respect to the carrier 14. Also, this configuration allows for collecting the tissue specimen while being cut.

Figure 4:
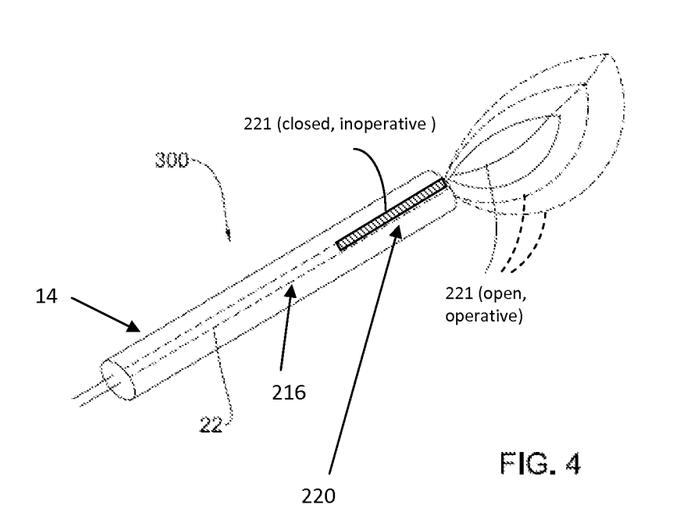

FIG. 4 shows a medical device 300 according to yet another example of the invention. Here, a treatment tool 216 has a body shaft 22 carrying at its distal end an excision element 220. The latter may or may not be integral with the body shaft 22. The excision element has a closed-loop cutting edge 221 which is pre-bent at fabrication so as to deploy from its inoperative closed position when inside the carrier 14 into an open ring-like shape when being projected from the carrier. Attached to the cutting edge 221 is a flexible tissue collecting unit. When the excision element is pushed (by user) out of the carrier 14 through its distal end, it gradually passes through its different operative states being of a spoon-like shape of different dimensions.

Figure 5:
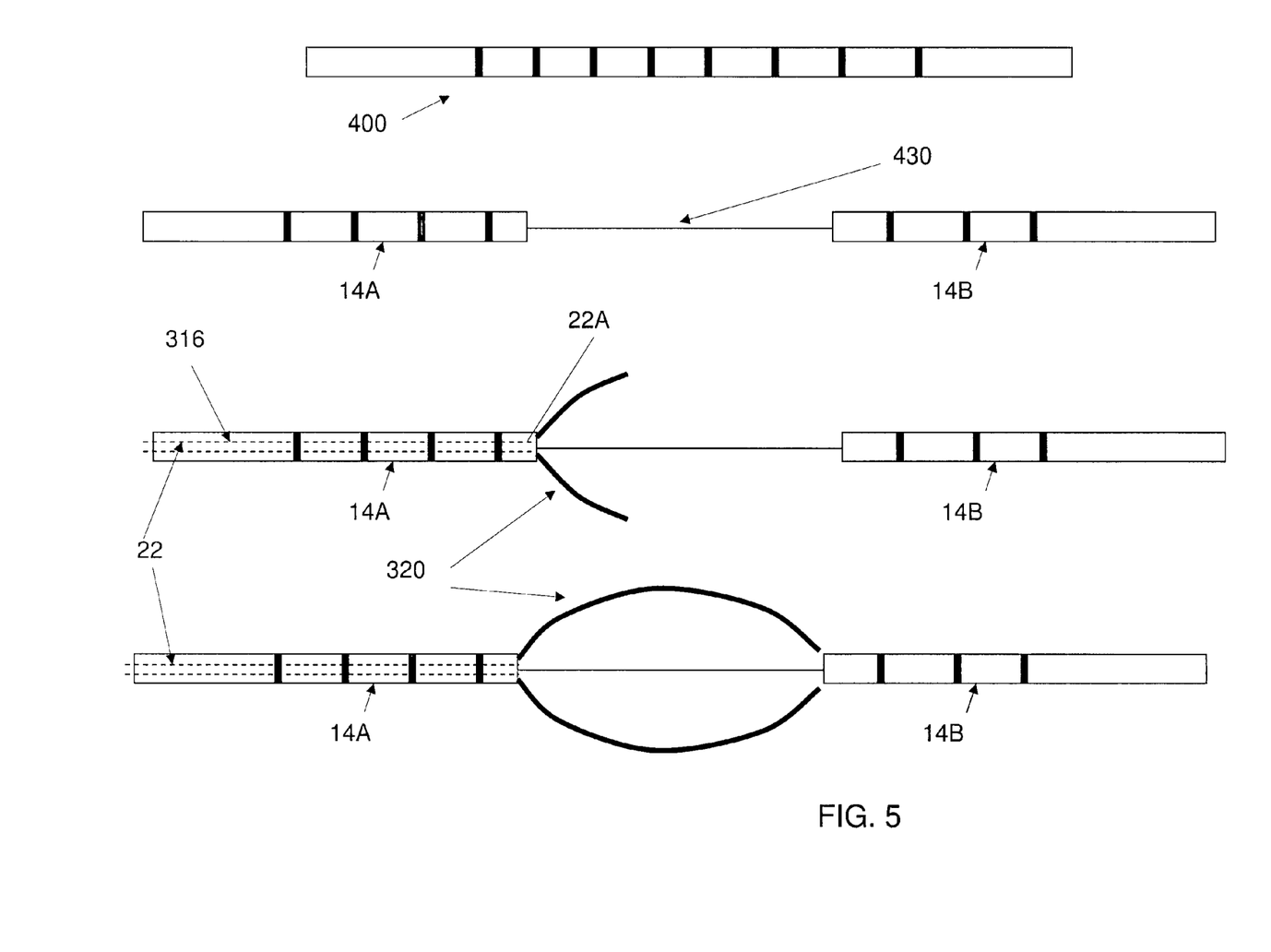

FIG. 5 shows a medical device 400 according to yet another example of the invention. Here, an elongated shaft (carrier) 14 is separable into two sections 14*a* and 14*b*, which remain connected to each other by a wire or shaft 430. A treatment tool 316 located inside the carrier 14 has a body shaft 22 carrying at its distal end 22A excision elements 320. The latter may or may not be integral with the body shaft 22. The treatment tool shaft 22 is advanced inside the shaft 14 until its distal end 22A reaches the distal end of the section 14A. Excision elements 220 are then deployed so as to excise an intact tissue portion.

Figure 6:
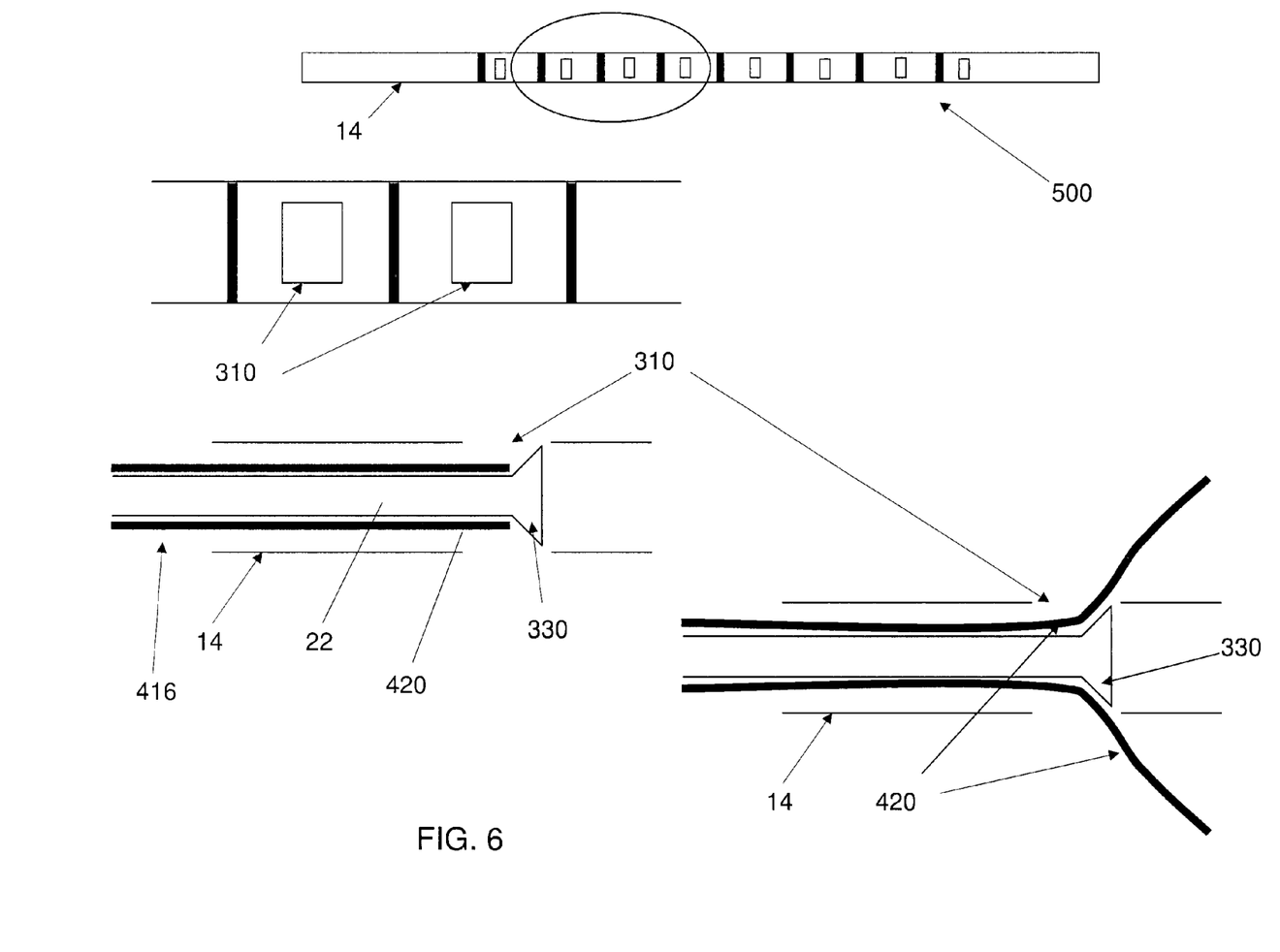

FIG. 6 shows a medical device 500 according to yet another example of the invention. Here, peripheral slots 310 are provided in the shaft/carrier 14 being interspaced between tissue characterization sensors. At each location along the shaft 14 there may be 2-8 peripheral slots. A treatment tool 416 has a body shaft 22 carrying at its distal end excision elements 420. The latter may or may not be integral with the body shaft 22. A number of excision elements 320 corresponds to the number of the slots 310. The treatment tool 416 is advanced inside the shaft 14 until its distal end is positioned at a specific slot 310 location. The distal end of the treatment tool shaft 22 has a tapered/angled ending portion 330. This ending portion allows for controlling an angle at which the excision elements 420 is extended from the shaft 14 into tissue. The excision elements 420 are pre-bent so that when extended they close back on the shaft 14, thus cutting the tissue portion adjacent to the shaft 14. Additionally, the excision elements 420 may be connected at their ends by wires, or other flexible connection. This connection can be manipulated to induce the contraction of the excision elements 420 towards shaft 14, to facilitate cutting of the tissue portion adjacent to the shaft 14.

It should be understood that in all the above-exemplified embodiments the device may be rotated, manually or mechanically, to assist in completer tissue treatment (e.g. cutting and removal).

Thus, the present invention provides a novel medical device capable of precisely located a tissue volume to be treated (removed), and also provides for treating (removing) the tissue by an integral medical device.

The invention claimed is:

1. A medical device configured to characterize and treat tissue, the device including a tissue characterization probe and a control unit communicating with the tissue characterization probe, the tissue characterization probe comprising:
    a carrier in the form of an elongated hollow shaft having a longitudinal axis defining a scanning axis of the probe during progression through a tissue mass, the elongated hollow shaft of the carrier having proximal and distal ends and an opening at the distal end defining an inner cavity extending on the longitudinal axis, and being configured to carry a body shaft of a treatment tool enabling controllable movement of the treatment tool within, out of and into the inner cavity on the longitudinal axis, such that a dimension or a location of a portion of the treatment tool projecting from the opening while the treatment tool moves on the longitudinal axis is controllably adjusted;
    a sensing arrangement mounted on an outer surface of the carrier, the sensing arrangement comprises an array of tissue characterization sensors of at least one of optical, radiofrequency (RF), microwave (MW), electrical and magnetic sensor types,
    the tissue characterization sensors in the array are arranged with a known distance between every two adjacent tissue characterization sensors in the array of the tissue characterization sensors at least along the longitudinal axis of the carrier,
    each of the tissue characterization sensors in the array is configured to generate tissue characterization signals from its successive locations during progression through the tissue mass surrounding the probe,
    wherein said control unit is preprogrammed to utilize said known distance between every two adjacent sensors, receive and analyze in real-time the tissue characterization signals from each sensor in the array, and generate in real-time tissue characterization output data comprising location and dimension of an abnormal tissue inside the tissue mass, said output data defining the dimension or location of the portion of treatment tool projecting from the inner cavity, on the longitudinal axis, to treat the abnormal tissue.

2. The device according to claim 1, further comprising a treatment tool comprising a body shaft, said treatment tool being carried within the inner cavity of the elongated carrier and configured to pass through said open distal end on the longitudinal axis, said treatment tool being configured and operable for utilizing the output data for consequent treatment of the abnormal tissue.

3. The device according to claim 2, wherein the treatment tool comprises at least one tissue treating portion, the treatment tool being configured and operable to be selectively shiftable between an inoperative position located entirely inside the carrier and an operative position at least partially projecting from the open distal end of the carrier such that the at least one tissue treating portion of the treatment tool is located outside the carrier.

4. The device according to claim 3, wherein the at least one tissue treating portion of the treatment tool projectable from the carrier has variable dimensions.

5. The device according to claim 3, wherein the at least one tissue treating portion of the treatment tool is movable with respect to the carrier on the longitudinal axis.

6. The device according to claim 3, wherein the treatment tool is configured to carry out at least one of the following: biopsy, cutting, delivering physical treatment, delivering treatment medication, and diagnostics.

7. The device according to claim 3, wherein the at least one tissue treating portion is configured as at least one tissue excision element.

8. The device according to claim 7, wherein the at least one excision element comprises a tissue collecting unit configured to collect tissue being removed.

9. The device according to claim 7, wherein the treatment tool comprises at least one excision element projectable from the body shaft.

10. The device according to claim 9, wherein the at least one excision element has first and second ends that are attached to respective first and second locations on the treatment tool body shaft and are spaced-apart from one another along the longitudinal axis of the carrier.

11. A device according to claim 10, wherein the treatment tool body extends along at least a part of the inside of the carrier such that at least one of the first and second locations is movable towards and away from the other along the longitudinal axis of the carrier to thereby adjust the dimension of a portion of the at least one excision element projecting from the carrier.

12. A device according to claim 10, wherein the treatment tool body has first and second members spaced-apart from one another along the carrier, the at least one excision element being attached by the first and second ends to facing one another edges of the first and second members, respectively, the movement of at least one of the first and second members with respect to the other resulting in a change in the dimension of a projecting portion of the at least one excision element.

13. A device according to claim 10, wherein the treatment tool body has an elongated member extending along at least a part of the carrier and being rotatable about the longitudinal axis of the carrier, the at least one excision element being attached by its opposite edge to the elongated member so as to rotate with the rotation of the elongated member, said the at least one excision element being configured and operable to vary its dimension at least along the longitudinal axis of the carrier.

14. A device according to claim 13, wherein the at least one excision element has a tissue collecting unit of variable dimensions.

15. The device according to claim 7, wherein the treatment tool is movable along the carrier such that a portion of the at least one excision element is selectively projectable from the carrier through a distal end of the carrier.

16. The device according to claim 15, wherein the treatment tool body shaft extends along the carrier and the at least one excision element is located at a distal end of the treatment tool body, the at least one excision element having a tissue cutting edge that is pre-bent into a certain closed-loop shape when the treatment tool is in said inoperative position and which is configured to gradually expand into a bent state of variable dimension when the treatment tool is in said operative position.

17. A device according to claim 9, wherein the carrier shaft is formed with slots interspaced between the tissue characterization sensors such that at each location along the carrier there are at least two peripheral slots.

18. A device according to claim 17, wherein the treatment tool body extends along at least a part of the carrier and is movable along the carrier, the treatment tool body carrying at its distal end a number of excision elements corresponding to the number of the slots, the number of excision elements being pre-bent such that they extend through the slots and close back towards the carrier, thus cutting a tissue portion adjacent to the carrier.

19. A device according to claim 18, wherein the number of excision elements are connected at their ends by flexible connectors, manipulation of the connectors inducing contraction of the number of excision elements towards the carrier, thereby facilitate cutting of the tissue portion adjacent to the carrier.

20. A device according to claim 18, wherein the distal end of the treatment tool body has a tapered ending portion, thereby allowing control of an angle at which the number of excision elements are extended from the carrier into tissue.

21. The medical device according to claim 1, wherein the control unit comprises a graphical user interface configured to present tissue type inside the tissue mass and said output data.

22. A medical device configured to characterize and treat tissue, the device comprising a tissue characterization probe and a control unit communicating with the tissue characterization probe, the tissue characterization probe comprising:
an elongated a carrier in the form of an elongated hollow shaft having a longitudinal axis defining a scanning axis of the probe during tissue characterization and treatment, the elongated hollow shaft of the carrier having proximal and distal ends and an opening at the distal end defining inner cavity extending on the longitudinal axis and being configured to carry a body shaft of a treatment tool configured to move on the longitudinal axis within, out of and into the inner cavity, such that a dimension and a location of a portion of the treatment tool projecting from the opening while the treatment tool moves on the longitudinal axis is controllably adjusted;
a sensing arrangement mounted on an outer surface of the carrier and configured for generating tissue characterization data with respect to a tissue mass surrounding the probe, the sensing arrangement comprises an array of tissue characterization sensors of at least one of optical, radiofrequency (RF), microwave (MW), electrical and magnetic sensor types, the array of tissue characterization sensors being arranged with known distance between every two adjacent sensors in the array at least along the longitudinal axis of the carrier,
wherein, for a given position of the probe, the tissue characterization data comprises an array of the tissue characterization signals about an array of locations along said longitudinal axis produced by the corresponding array of the tissue characterization sensors at said known locations between them, the tissue characterization signals from each of the tissue characterization sensors in the array and the known distances between the tissue characterization sensors providing data concerning location and dimension of an abnormal tissue inside the tissue mass,
wherein, said control unit is preprogrammed to utilize said known distance between every two adjacent sensors, receive and analyze in real-time the tissue characterization signals from each sensor in the array, and generate in real-time tissue characterization output data comprising location and dimension of an abnormal tissue inside the tissue mass, and
wherein the treatment tool comprises said body shaft and at least one tissue treating portion configured to treat the abnormal tissue, the treatment tool being configured to be inserted in the inner cavity of the carrier and to be operable in accordance with the location data to be selectively shiftable between an inoperative position of the treatment tool located entirely inside the inner cavity of the carrier and an operative position of the treatment tool at least partially projecting from the inner cavity of the carrier such that the at least one tissue treating portion is located outside the carrier.

23. A medical device configured to characterize and treat tissue, the device a tissue characterization probe and a control unit communicating with the tissue characterization probe,
the tissue characterization probe comprising:
a carrier in the form of an elongated hollow shaft having a longitudinal axis defining a scanning axis of the probe during the tissue characterization and treatment, the elongated hollow shaft of the carrier having proximal and distal ends and an opening at the distal end defining an inner cavity extending on the longitudinal axis and being configured to carry a predetermined treatment tool and to enable controllable movement of the treatment tool on the longitudinal axis, within, out of and into the inner cavity;

a sensing arrangement mounted on an outer surface of the carrier and configured for generating tissue characterization data with respect to a tissue mass surrounding the probe, wherein the sensing arrangement comprises an array of tissue characterization sensors of at least one of optical, radiofrequency (RF), microwave (MW), electrical, and magnetic sensor types, the array of tissue characterization sensors being arranged in a spaced-apart relationship with a known distance between every two adjacent sensors in the array at least along the longitudinal axis of the carrier, wherein, for a given position of the probe, the tissue characterization data comprises an array of the tissue characterization signals about an array of locations along said longitudinal axis produced by the corresponding array of the tissue characterization sensors at said known locations between them, and said control unit is preprogrammed to utilize said known distance between every two adjacent sensors, receive and analyze in real-time the tissue characterization signals from each sensor in the array, and generate in real-time tissue characterization output data comprising location and dimension of an abnormal tissue inside the tissue mass, and wherein the treatment tool is configured to remove the abnormal tissue, the treatment tool comprising at least one excision element and being configured to be inserted into the inner cavity of the carrier and to be operable in accordance with the output data to be selectively shiftable between an inoperative position of the treatment tool located entirely inside the inner cavity of the carrier and an operative position of the treatment tool at least partially projecting from the inner cavity of the carrier such that at least a part of the at least one excision element is located outside the carrier.

24. The medical device of claim 23, wherein said at least part of the excision element located outside the carrier having variable dimensions.

\* \* \* \* \*